United States Patent [19]
Houser

[11] Patent Number: 5,865,801
[45] Date of Patent: Feb. 2, 1999

[54] MULTIPLE COMPARTMENTED BALLOON CATHETER WITH EXTERNAL PRESSURE SENSING

[76] Inventor: Russell A. Houser, 4572 Maureen Cir., Livermore, Calif. 94550

[21] Appl. No.: 503,843

[22] Filed: Jul. 18, 1995

[51] Int. Cl.⁶ ................................................ A61M 29/00
[52] U.S. Cl. ................................ 604/96; 604/22; 604/98; 606/108; 606/194; 607/97; 607/101; 607/105; 600/488; 600/587; 600/505
[58] Field of Search .......................... 604/20, 96, 97–99, 604/101–2, 104, 113–4, 22; 606/191–2, 194–5, 198, 108; 607/98–9, 113, 97, 101, 99, 104, 105; 128/640, 656, 658, 660.01, 660.02, 662.06, 673, 675, 748; 600/433, 435, 437, 438, 442, 486, 488, 561, 481, 483, 485, 487, 490, 493, 495, 497, 499, 500, 502, 504, 505

[56] References Cited

U.S. PATENT DOCUMENTS

| | | |
|---|---|---|
| 3,710,781 | 1/1973 | Huthcins, IV, et al. . |
| 4,030,481 | 6/1977 | Hill ............................................ 128/2 |
| 4,040,413 | 8/1977 | Ohshiro . |
| 4,554,927 | 11/1985 | Fussell .................... 128/670 |
| 4,787,388 | 11/1988 | Hofmann . |
| 4,878,495 | 11/1989 | Grayzel . |
| 4,983,165 | 1/1991 | Loiterman . |
| 5,135,001 | 8/1992 | Sinofsky et al. ................... 128/662.06 |
| 5,146,788 | 9/1992 | Raynes . |
| 5,190,540 | 3/1993 | Lee . |
| 5,236,413 | 8/1993 | Feiring ...................... 604/21 |
| 5,267,959 | 12/1993 | Forman . |
| 5,275,169 | 1/1994 | Afromowitz et al. . |
| 5,292,321 | 3/1994 | Lee . |
| 5,304,132 | 4/1994 | Jang ....................... 604/192 |
| 5,304,135 | 4/1994 | Shonk . |
| 5,308,323 | 5/1994 | Sogawa et al. ........................... 604/96 |
| 5,308,356 | 5/1994 | Blackshear, Jr. et al. . |
| 5,380,319 | 1/1995 | Saito et al. ............................... 604/96 |
| 5,435,308 | 7/1995 | Gallup et al. ........................... 128/634 |
| 5,439,446 | 8/1995 | Barry ....................................... 604/96 |
| 5,443,470 | 8/1995 | Stern et al. .............................. 607/98 |
| 5,501,667 | 3/1996 | Verduin, Jr. ............................. 604/96 |
| 5,505,730 | 4/1996 | Edwards .................................. 604/21 |

*Primary Examiner*—Ronald K. Stright, Jr.
*Attorney, Agent, or Firm*—Frederick W. Niebuhr

[57] ABSTRACT

A balloon catheter includes an elongate pliable catheter tubing with a dilatation balloon fixed to the catheter tubing near its distal end. The dilatation balloon includes a first wall for dividing the balloon into a plurality of dilatation compartments adjacent one another and arranged angularly about the catheter tubing. Each dilatation compartment is fluid tight and in fluid isolation from other compartments. The compartments are individually controlled so the pressure within each balloon compartment may be adjusted as determined by the operator. The dilatation balloon includes a second wall composed of the respective outer wall portions of the dilatation compartments which defines an outer transverse profile of the dilatation balloon and adapted to form surface engagement with the tissue segments surrounding the balloon when the compartments are dilatated. The exterior surface of the balloon dilatation compartments include pressure sensing apparatus mounted thereon and adapted for positioning between the second wall and the tissue wall segment during surface engagement for measuring the pressure between the dilatation balloon and the tissue wall segment. The balloon compartments are individually controlled so the pressure within each balloon compartment may be adjusted by the operator. Alternative embodiments include thin film heating elements located on the exterior surface, thin film transducers having an ultrasonic imaging capability located on the exterior surface, drug delivery capabilities and a dual balloon arrangement.

49 Claims, 7 Drawing Sheets

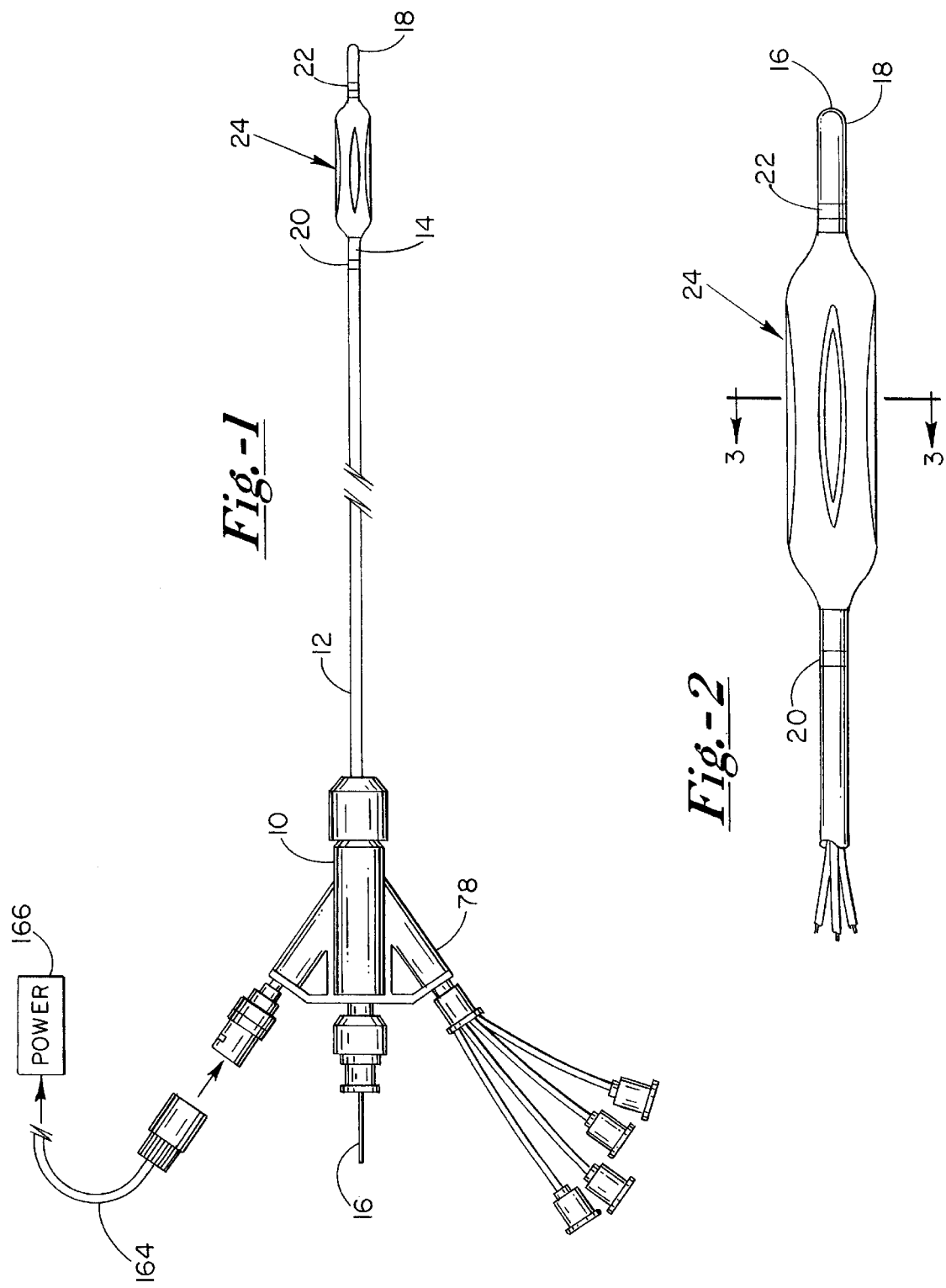

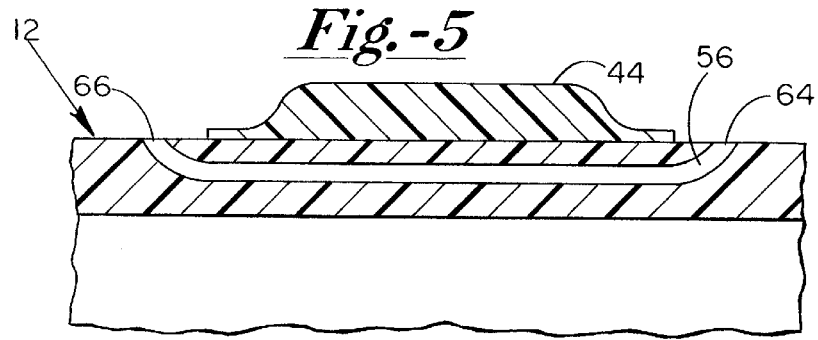
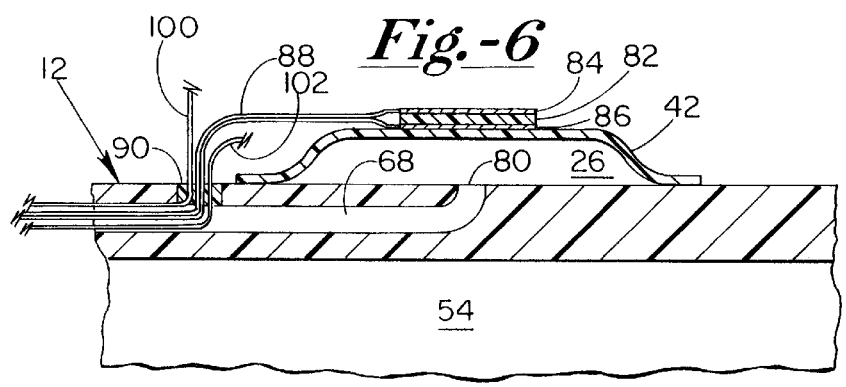
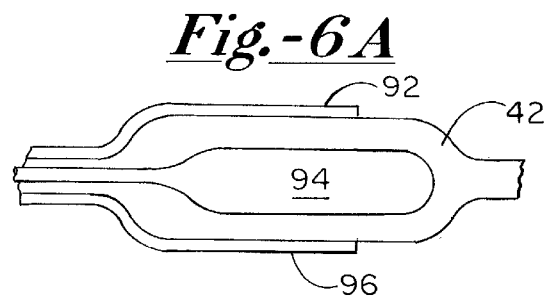
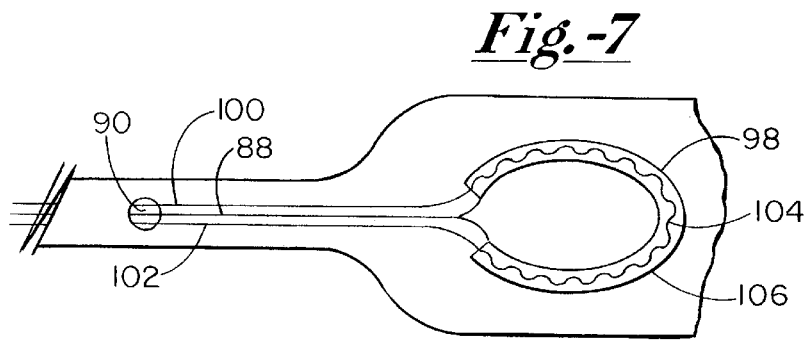

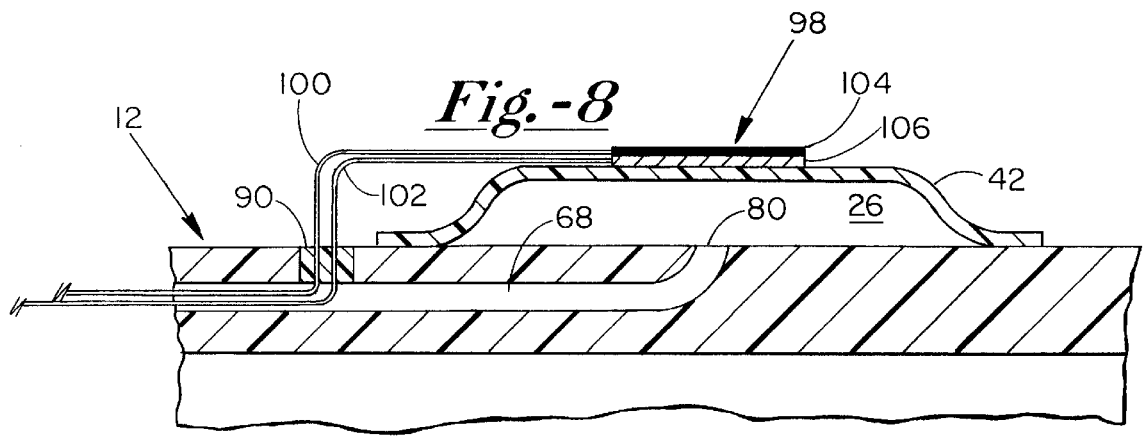
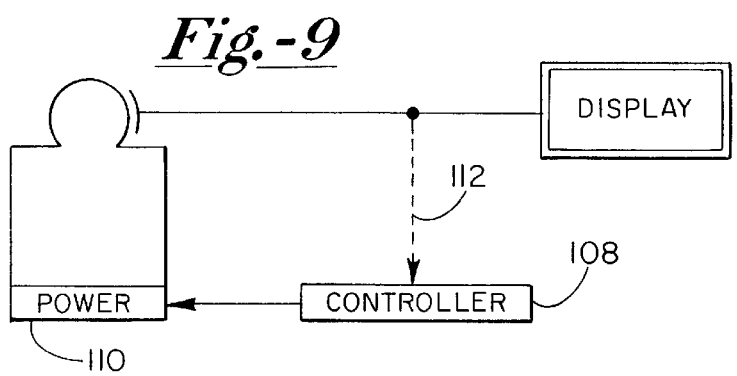
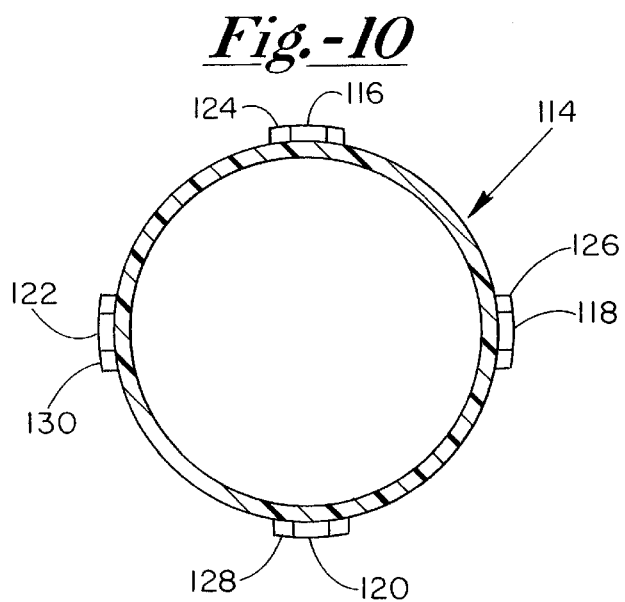

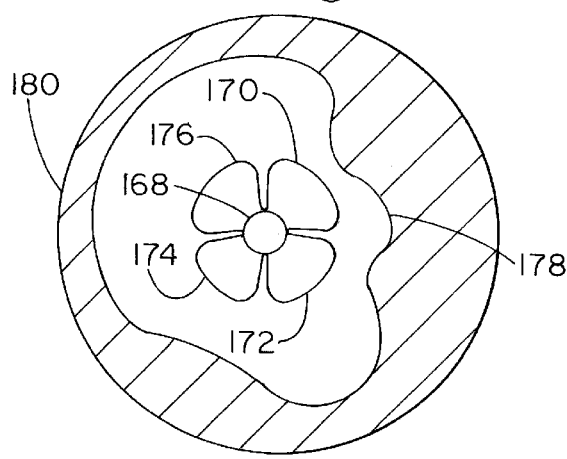
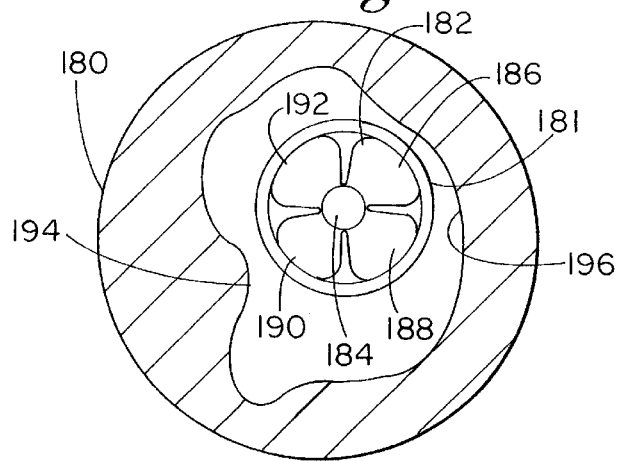
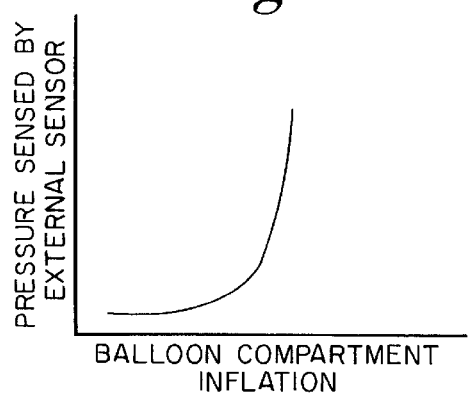
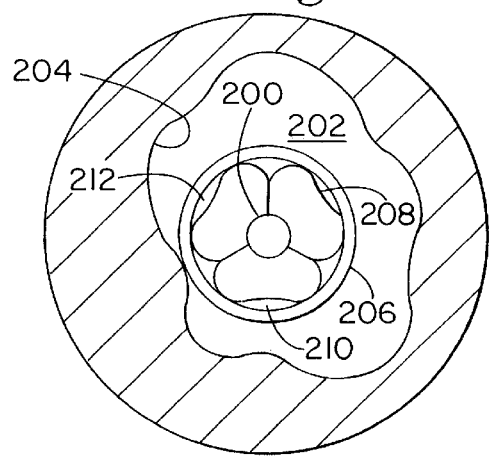

MULTIPLE COMPARTMENTED BALLOON CATHETER WITH EXTERNAL PRESSURE SENSING

FIELD OF THE INVENTION

The present invention relates to devices positionable in body cavities for treatment or viewing and in particular to angioplasty catheters, especially for coronary and peripheral arteries.

BACKGROUND OF THE INVENTION

Balloon catheters are well known for their utility in treating certain types of obstructions or occlusions in blood vessels, such as plaque build up. Angioplasty catherization typically involves aligning a balloon catheter within the vessel to position its dilatation balloon at or along the obstruction. Then, fluid under pressure is supplied to the balloon through a balloon inflation lumen in the catheter, expanding the balloon against the obstruction.

Balloon angioplasty catheters have been around since the late 1970s. Since that time the efficacy for the procedure has not significantly been improved. The restenosis rate for PTCA (angioplasty) has always averaged about 40 percent. Overinflation of the balloon can cause cracks in the intimal layer of an artery, allowing smooth muscle cell proliferation. Furthermore, overinflation of the balloon is a major cause of restenosis. In extreme cases, an aneurysm or perforation of the vessel can result from overinflation.

Overinflation of balloon catheters arises from several factors. One factor is the variety of plaque hardnesses. Atherosclerotic disease in an artery can result in plaque deposits having a wide range of hardness from "scrambled eggs" to bone. Another factor is that the profile of the obstruction is generally eccentric within the artery and does not conform to the concentric dilatation balloon profile. The physician can monitor the pressure on the inside of the balloon, but not the pressure between the outside of the balloon and the inside wall of the artery. As a result, overinflation can occur because of the concentric configuration of the balloon and the inability to assess the pressure between the outside of the balloon and the inside wall of the artery. The fluid pressure inside the inflating balloon cannot alert the physician to excessive pressure between the external surface of the balloon and the arterial wall.

The application of heat to the vessel wall during the angioplasty procedure appears to have a positive effect by requiring less force to compress the plaque against the arterial wall. Conventional balloon catheters do not provide an effective means for heating vessel walls during an angioplasty procedure. Stents are also employed in arteries. However, it is difficult to determine when the stent has been fully deployed and is in contact with the vessel wall. Current angioplasty catheters do not provide a reliable means for the physician to determine if a stent is fully deployed.

Therefore, it is an object of the present invention to provide an angioplasty balloon adapted to allow a physician to conform the balloon to an artery's inner profile, and further avoid overinflation of the balloon.

Another object of the present invention is to provide an angioplasty catheter with individually inflatable dilatation compartments that allow the balloon to assume an eccentric shape and apply different localized pressure to the different regions of surrounding artery.

A further object of the present invention is to provide an angioplasty catheter with pressure sensing capability on the balloon's external surface for monitoring pressure between the balloon and artery tissue allowing the catheter to be adaptable to treat different plaque hardnesses and to avoid overinflation.

Another object of the present invention is to provide an angioplasty balloon catheter which may be utilized for deployment of a plastically deformable stent and for controllably expanding the stent toward a custom fit to an eccentric arterial profile.

Yet another object of the present invention is to provide an angioplasty balloon catheter having thin film heaters on the outside of the dilatation balloon to allow the physician to heat the obstructed area during the angioplasty procedure, or to deploy and expand recovery metal stents by locally heating a treatment site within an artery.

A further object of the present invention is to provide an angioplasty balloon catheter with film transducers on the balloon's external surface to provide a means of intra vessel imaging.

Still another object of the present invention is to provide an angioplasty balloon catheter with perfusion lumens extending through the catheter shaft with a port located adjacent the proximal end of the balloon and another port located adjacent the distal end of the balloon, thereby allowing fluid to flow past the catheter when the balloon is expanded and in contact with the arterial inner surface.

Yet another object of the present invention is to provide dual balloon angioplasty catheter with the distal balloon opening the occlusion and the proximal balloon for deploying a stent, intra vessel ultrasonic imaging or delivering a drug to the lesion site.

SUMMARY OF THE INVENTION

To achieve these and other objects there is provided a device for performing a balloon angioplasty procedure. The device includes an elongate catheter having a proximal end and a distal end. A dilatation balloon is fixed to the catheter tubing near the distal end and extends substantially longitudinally along the catheter tubing. The catheter is flexible and maneuverable with a guide wire to locate its distal tip within a body lumen and place the dilatation balloon within the obstructed area. Radiopaque markers on the catheter shaft under the working area of the balloon assist in positioning the balloon in the artery.

The balloon has a plurality of dilatation compartments adjacent one another and arranged angularly about the catheter tubing. Fluid under pressure is individually supplied to the various dilatation compartments. Each compartment is fluid tight and isolated from the other compartments. The balloon dilatation means which supplies the fluid under pressure to the various dilatation compartments is controllable to alter the dilatation pressure to a value different than the nominal pressure in at least one of the compartments while maintaining the dilatation pressure at the nominal value in a second selected compartment. This allows the physician to controllably alter the balloon profile away from the nominal shape and toward conformity with the tissue wall profile of the tissue wall segment.

The catheter tubing additionally may include at least one perfusion lumen open to the exterior of the catheter tubing at first and second locations proximal and distal relative to the balloon, respectively. When the balloon is dilated into surface engagement with the surrounding tissue wall segment, it prevents passage of fluids along the catheter tubing. Thus, the perfusion lumen allows fluid passage during the angioplasty procedure.

The balloon catheter can include a pressure sensing means mounted on the exterior wall of the balloon, to measure the pressure between exterior surface of the dilatation balloon and the tissue wall segment. Preferably, the pressure sensing means includes a plurality of piezoelectric pressure transducing thin films or fluid filled pressure sensing tubes. A piezoelectric pressure transducing thin film or fluid filled pressure sensing tube is preferably bonded to each outer wall of the dilatation compartments. The pressure sensing means is coupled to a power source at the proximal end. A display means is operably connected to the sensors to display the pressure between the artery wall and the balloon's exterior surface.

The balloon catheter additionally can have thin film heating elements on the outside of the balloon surface. These are preferably bonded to the outer wall of each dilatation compartment and are connected to a power source and display means at the proximal end of the catheter. The temperature may be monitored and adjusted during the angioplasty procedure to heat adjacent tissue or deploy a stent formed of a recovery metal or thermoset plastic.

The balloon catheter additionally may include piezoelectric ultrasonic transducers on the balloon's exterior surface allowing the physician to utilize ultrasound to position the catheter and to view the vessel surface surrounding the catheter. The piezoelectric thin film transducers used as pressure sensors also can be alternatively used as ultrasonic transducers. The piezoelectric thin film transducers are coupled to a control which adjusts the signal to films for pressure sensing or ultrasound imaging.

Another embodiment of the balloon catheter incorporates two balloons at the distal end of the catheter. The first balloon on the distal end is utilized to enlarge the occluded area. The second balloon, located just proximally from the distal balloon, can be utilized for stent deployment or drug delivery. The drug delivery portion of the balloon is indented and perforated. The two balloons can employ the pressure sensors, ultrasonic transducers and heating elements on their exterior surfaces. Radiopaque marks are located on both balloons or between to allow the physician to position the balloons in the occluded area.

IN THE DRAWINGS

For further understanding the above features, advantages, reference is made to the following detailed description and to the drawings in which:

FIG. 1 is an elevational view of a balloon catheter device constructed in accordance with the present invention;

FIG. 2 is an enlarged view of the distal region of the balloon catheter of FIG. 1;

FIG. 5 is a sectional view of the interior wall taken along line 6—6 in FIG. 3;

FIG. 6 is a sectional view of the thin film transducer on the distal end of the catheter taken along line 5—5 in FIG. 3;

FIG. 6a is an enlarged view of the distal region of an alternative embodiment of a pressure sensor.

FIG. 7 is a sectional view of an alternative embodiment of a pressure sensor;

FIG. 8 is a enlarged view of the heating and pressure sensing elements of the balloon catheter;

FIG. 9 is a schematic view illustrating circuitry for providing an electrical current through a mounted heating element on the balloon;

FIG. 10 is a cross sectional view of a first alternative embodiment for the balloon configuration;

FIG. 12 is a diagramic view illustrating use of the device;

FIG. 13 is a diagramic view illustrating the use of first alternative embodiment for deploying a stent;

FIG. 14 is a graph representation of the pressure change before and after tissue contact from the balloon surface;

FIG. 15 is a diagramic view illustrating the use of the balloon catheter for deploying a shape memory metal stent.

DETAILED DESCRIPTION OF THE PREFERRED EMBODIMENTS

Figure 3:
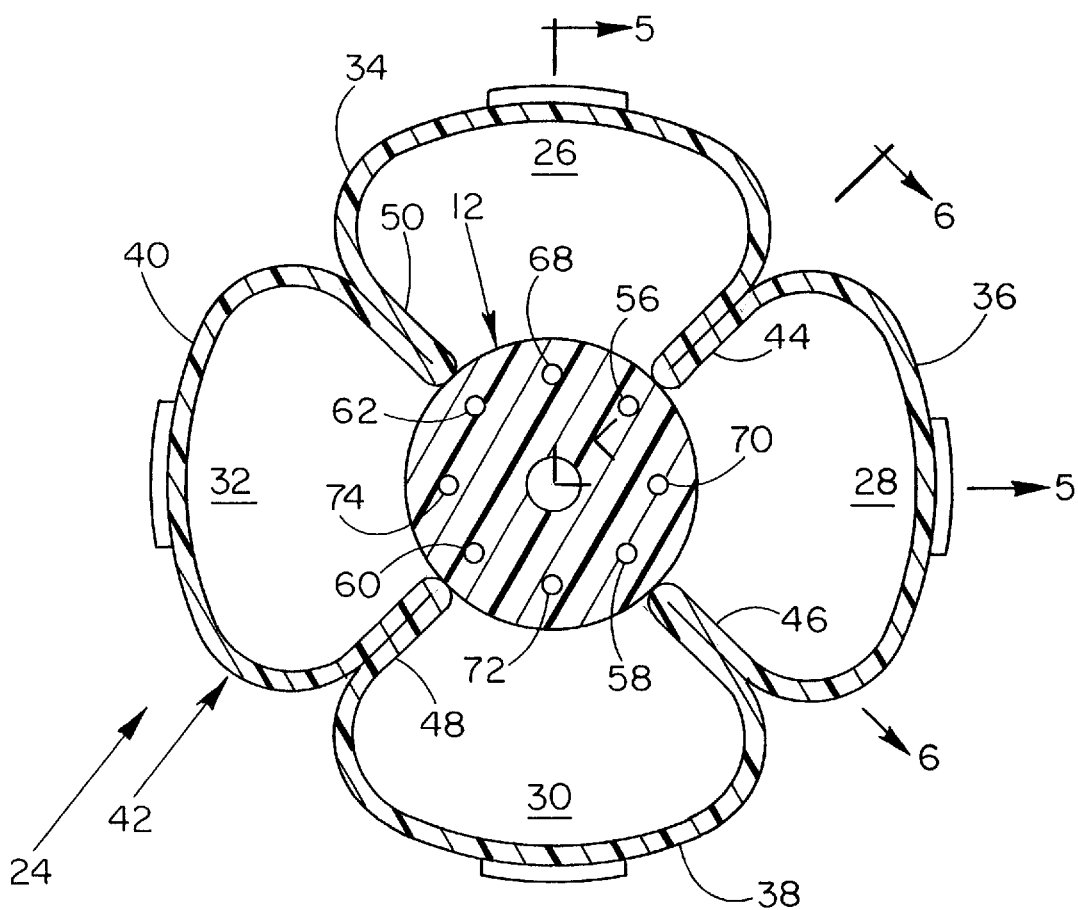
FIG. 3 is a cross sectional view of the balloon catheter showing the balloon profile.

Turning now to the drawings, there is shown in FIG. 1 a balloon catheter device for treating obstructions in body lumens, more particularly blood vessels. The device includes a proximal adaptor 10 and an elongated pliable catheter 12 connected at its proximal end to the proximal adaptor 10 and a dilatation balloon 24.

The catheter 12 is formed of a biocompatible polymer such as polyamide/nylon blend, Pebax (brand name), polyether block amides, Pellethane (brand name) polyurethane, polyamide or other polymer resin, and can have an outside diameter in the range of 3 Fr. (1 mm.) To 8 Fr. (2.7 mm.) or larger. The catheter shaft may be braided and unbraided and includes several lumens that run axially from proximal adaptor 10 to a distal end region 14. A guide wire 16 contained within the catheter extends proximally beyond proximal adaptor 10 and distally beyond the tapered distal tip 18 of the catheter 12. The guide wire lumen preferably has an inner diameter of 0.012 inches. Alternatively a steerable catheter may be used and the appropriate lumens or other steering control means are incorporated into the catheter shaft. Further lumens are provided in the catheter for balloon inflation which additionally carry leads connected to the pressure sensors and thin film heaters as will be explained later. Additionally, perfusion lumens are included to allow blood to bypass the inflated balloon in the artery by means of ports in the shaft of the catheter located proximal and distal of the balloon. The balloon section of the catheter additionally has radiopaque markers 20 and 22 on the catheter shaft proximal and distal the balloon to allow the physician to align the balloon section within the vessel lesion.

A dilatation balloon 24 is formed to extend axially along distal end region. The balloon has several longitudinal compartments 26, 28, 30 and 32 all angularly adjacent one another and cooperating to surround the catheter as seen in FIG. 3. The compartments have radially outward wall segments 34, 36, 38, and 40 that cooperate to provide a continuous outer wall 42 for the balloon 24 and are adapted to engage a tissue wall segment of the vessel over substantially the balloon's entire surface area. Interior walls 44, 46, 48 and 50 angularly divide the balloon 24 into the plurality of the dilatation compartments adjacent one another and arranged angularly about the catheter tubing. As seen in FIG. 3, each compartment extends approximately 90° angularly or circumferentially about the catheter tubing. Each of the compartments is fluid tight and in fluid isolation from the other compartments. As one skilled in the art can appreciate, balloon 24 can be constructed to have any desired number of dilatation compartments and the balloon preferably has an outer diameter of 3 mm when it is inflated about the catheter shaft. The balloon material may be made of a compliant material such as polyethylene or polyurethane. Alternatively, it may be an inextensible material such as nylon, PET and polyamide. Furthermore, the balloon assembly is coated with a biocompatible coating such as Parylene®.

Figure 4:
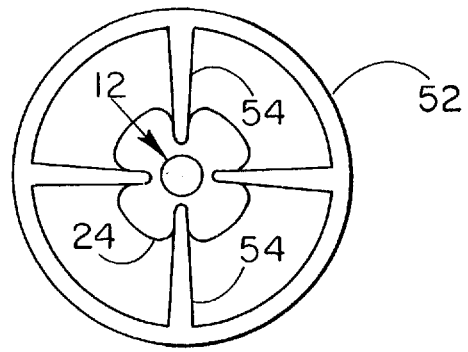
FIG. 4 is an end view of the multi-compartment balloon being formed.

The interior balloon walls are formed by two overlapping layers of the balloon material. The four compartment balloon 24 is constructed by using a clip 52 with four prongs 54 for drawing portions of an inflated balloon against the outside surface of catheter 12 as shown in FIG. 4. Another method of construction is to create one balloon with interior walls of single thickness. For example, the balloon can be blown inside of a glass mold with the desired configuration.

The catheter has perfusion lumens 56, 58, 60 and 62 which extend through the catheter shaft at the area the dilatation balloon is located. The perfusion lumens preferably have a diameter of 0.010 inches. As shown in FIG. 5, perfusion lumen 56 adjacent wall 44 extends through the catheter shaft from a port 64 located distal of the balloon 24 to a port 66 located proximal the balloon. Thus, when the balloon is inflated and in surface contact with the arterial wall, blood is able to bypass the blocked area through the perfusion lumens. Fluid under pressure is supplied to the balloon compartments by balloon inflation lumens 68, 70, 72 and 74 which extend axially through the catheter and are shown associated with their respective dilatation chambers in FIG. 3. These lumens are preferably 0.012 inches in diameter and they are coupled to a fluid source 76 via branch 78 on the proximal adaptor 10. Each balloon chamber is inflated by a separate inflation device such as ACS's Indeflator (brand name), a multi port manifold or equivalent device. The inflation lumens are open to the balloon interior under each balloon chamber adjacent the catheter to allow the inflation fluid to enter and exit. FIG. 6 shows inflation lumen 68 perforated at 80 for fluid communication with balloon compartment 26.

Located on the exterior wall of the multi compartment balloon is pressure sensing means, preferably several piezoelectric thin film pressure transducers. The transducers, generally around 0.003' thick, are bonded by any suitable adhesive to the apex of each balloon compartment. A bifilar wire is coupled to each piezoelectric pressure sensor and extends through the catheter in an associated one of balloon inflation lumens to an electrical connector located on the handle. FIG. 6 is an enlarged view of pressure sensor piezoelectric film 82 which has on opposite sides a first electrode 84 and second electrode 86. A small gage bifilar wire 88, (44 awg, for example), provides a wire for each of electrodes 84 and 86 on the thin film sensor 82. Bifilar wire 88 is inserted into the associated inflation lumen 68 through a hole in the catheter shaft 12. The hole is sealed after the wire has been loaded into the catheter shaft, as indicated at 90. The bifilar wire may alternatively be inserted through a hole in the balloon outer wall 42 and into the associated inflation lumen. The hole is sealed after the wire is loaded into the balloon.

Piezoelectric sensors work by generating a measurable voltage when force is applied to them. Thus, the pressure between the balloon outer surface and the vessel wall can be determined by converting the voltage to a pressure value. As the pressure changes, the voltage of the piezoelectric thin film also changes.

The thin film piezoelectric transducers can also be used for ultrasonic imaging of the catheter within the vessel at the obstructed areas. Bifilar wire 88 coupled to transducer electrodes 84 and 86 can be used for inducing the desire oscillation in sensor 82. The use of piezoelectric thin films as ultrasound traducers is known to those skilled in the art. If the transducers are to be used in ultrasonic imaging, they are employed in concert as a phased coupled array. The transducers to be used in the ultrasonic imaging can be bonded directly to the catheter shaft, or the outside of the balloon and employed in concert as a phased coupled array. The following two articles and product specification sheet note the use of thin film transducers as ultrasonic imaging and they are incorporated by reference herein: Brown, Lewis F. and Carlson, David L., *Ultrasound Transducer Models for Piezoelectric Polymer Films,* IEEE Transaction on ultrasonics, Ferroelectrics and Frequency Control, Vol. 36, No. 3, May 1989; Richard L. Goldberg, Stephen W. Smith and Lewis F. Brown, *In Vivo Imaging Using a Copolymer Phased-Array* and AMP Corporation's Summary of Operating Properties: DTI-028K for Kynar® Piezo Film (© 1993 01 Mar. 1994 rev. C).

An alternative embodiment for sensing the pressure between the balloon's exterior surface and the arterial wall consists of small compliant enclosed pressure tubes, shown at 92, 94, and 96 in FIG. 6A. The tube is preferably oval and its distal end is sealed and bonded to the apex of each balloon compartment. The tube, preferably made from polyurethane, then continues along the catheter shaft either on the outside or the inside (e.g., an inflation lumen) terminating at the proximal adaptor where it is coupled to a digital pressure measuring device. The tube is filled with air, a contrast fluid or saline. When the balloon surface comes into contact with the lesion or arterial wall, the compliant tube deforms, changing the pressure within the tube.

Catheter 12 includes thin film heaters attached to the exterior of the balloon adjacent and surrounding the piezoelectric sensors. The thin film heaters are preferably made from a polyamide sheet with a thin resistive coating pattern, e.g., nickel, sputter coated onto the surface. The thin film heaters, one of which is shown at 98 in FIGS. 7 and 8, is connected to a bifilar lead wire 100 and to a thermocouple wire 102 to monitor the temperature. Bifilar lead wire 100 is connected to the opposite ends of a thin film heating element 104 formed on a dielectric sheet 106 of the heater. Thermocouple wire 102 is connected to the thin film heater near the heating element. The leads and thermocouple wire are inserted into the balloon inflation lumen 68 through a hole in the catheter shaft. Alternatively, the leads and thermocouple can be inserted through a hole in the balloon wall and then loaded into the inflation lumen. As previously noted, the hole is sealed once the wires have been loaded into the catheter (see FIG. 6 at 90)shaft or balloon. The wires extend through inflation lumens the length of the catheter and terminate in the electrical connector on a control panel 107.

An RF circuit for heating of the thin film is schematically illustrated in FIG. 9. A controller 108 adjusts power from a supply 110 as required for generating current through heating element 98 in an amount selected to heat the thin film to the predetermined temperature. A broken line at 112 indicates that if desired, the output of thermocouple 102 can be employed to automatically adjust the heating element current.

FIG. 10, a cross section shows an alternative balloon 114 configured with only one balloon inflation chamber. The balloon incorporates four pressure sensors 116, 118, 120, and 122 and four thin film heaters 124, 126, 128 and 130 on the exterior surface in a circumferentially or angularly spaced apart arrangement around the exterior of the balloon. Thus, a variety of arrangements of the pressure sensors, film heaters and dilatation compartments are possible.

Figure 11:
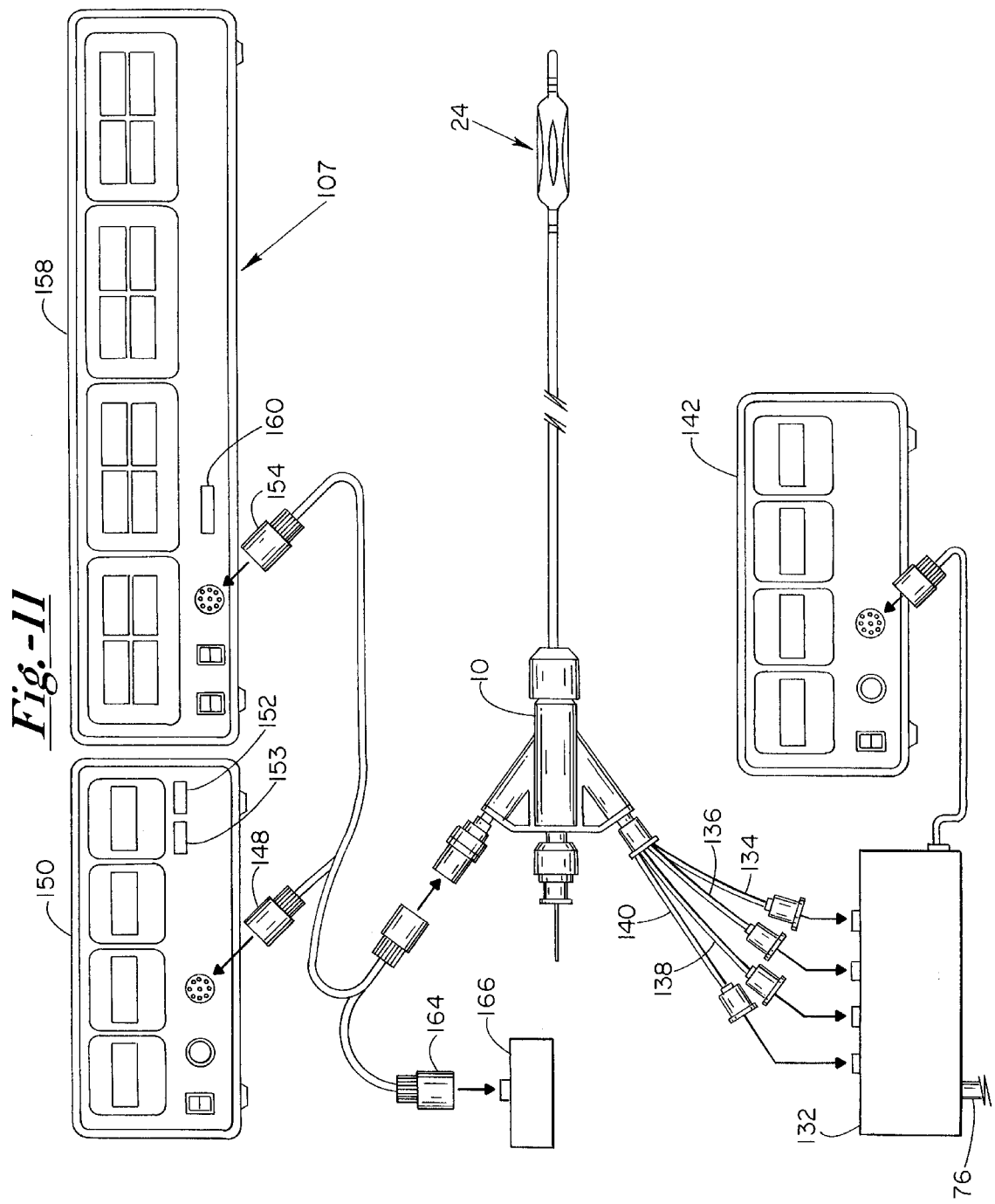
FIG. 11 is a schematic of the control panel for use with the present invention.

The catheter system includes a control center 107 (FIG. 11). The control center incorporates and thereby functions as a multiplexing means for monitoring and controlling the piezoelectric thin film transducers, the inflation of the dilatation compartments, and temperature of the thin film heaters. The pressure control consists of a manifold 132, fluid supply 76 and fluid tubes 134, 136, 138 and 140 coupled to the proximal adaptor 10 for supplying the fluid through the inflation lumens. A display 142 displays the internal pressure in the dilatation chambers.

The bifilar leads (e.g., 88) from the thin film transducers exit the inflation lumens and are coupled at 148 the control center. The pressure between the balloon's outer wall and each tissue wall sensed by the piezoresitive sensor is determined by the voltage of the piezoelectric thin film. A display 150 reads the voltage from each piezoelectric sensor, converts it and displays the pressure reading. If a compliant pressure sensing tube is used instead of thin film transducers, the control panel includes a digital pressure measuring device which reads the pressure change within the tube, converts it and displays the reading.

If ultrasonic imaging is desired, the piezoelectric thin film transducers sensors are adjusted by selecting ultrasonic mode at switch 152 on the control panel 150 and using a control 153 to accomplish the ultrasonic imaging. The appropriate ultrasonic imaging screen is additionally coupled to the control center.

The bifilar leads 100 from the heating element and the thermocouple wires 102 exit the inflation lumens and are coupled to the control center at 154. A display 158 shows the temperature at the selected thin film heater and a control 160 allows the temperature to be adjusted. Thus, the thermocouple senses the temperature of the thin film and provides the corresponding temperature reading at display 158. If the display 158 indicates a need to increase or decrease the temperature, controller 160 is adjusted to alter the current accordingly.

The bifilar leads exit the inflation lumens (not shown) at the proximal adaptor to couple the control center 107 to the proximal adaptor 10 as indicated above. The proximal adaptor 10 additionally includes an electrical connector 164 (FIG. 1) located at the proximal end. The electrical connector is coupled to a power source 166. The power supply is preferably an RF source, but can be a DC source.

The balloon 24 of the present invention can be used for balloon angioplasty, stent deployment and other procedures. As shown in FIG. 12, a catheter balloon 168 having four dilatation compartments 170, 172, 174 and 176 is inserted in the vessel 180 until it reaches the obstructed area. Radiopaque markers on the catheter shaft under the balloon 168 assist the physician in positioning the balloon adjacent an obstruction 178. The multiple compartments of the balloon are then inflated to contact the obstruction. As the balloon is inflated, the pressure sensed by the piezoelectric sensors on balloon compartments 170 and 172 may be greater because the hardness of obstruction 178. Alternatively, the obstruction 178 may have a yielding consistency and the pressure would be less. Thus, when viewing the control display 142, the physician is able to vary the pressure as necessary and adapt the balloon catheter to the specific requirements of the obstruction, and overinflation is avoided.

The balloon catheter may additionally be used in stent deployment. As shown in FIG. 13, a plastically expandable stent 181 substantially surrounds a balloon 182 of a catheter 184. This balloon has four dilatation compartments 186, 188, 190 and 192. Once the balloon 182 and stent 181 are located at the appropriate location within the vessel 180 and adjacent the obstruction 194, the balloon compartments 186-192 are inflated to deform the stent 181 into contact with the obstruction 194. The physician is able to control stent deployment by adjusting the inflation of the balloon dilatation compartments as necessary. Greater inflation may be required for dilatation compartments 190 and 192 than compartments 186 and 188. Thus, compartments 190 and 192 can be monitored so that over inflation (that could cause vessel damage) in the obstructed area 196 would be avoided. Furthermore, by viewing the pressure between the artery wall and balloon with regard to the balloon inflation pressure, the physician can determine that the stent is fully deployed.

The graph in FIG. 14 represents the inflation vs. external pressure curve. Once the stent and balloon contact the artery wall, the curve becomes non-linear. Once the stent has been deployed, the balloon catheter is deflated and withdrawn from the vessel.

The use of the embodiment incorporating thin film heaters can assist both in balloon angioplasty procedures and in deployment of shape memory metal stents such as those made of Nitinol. Additionally, other stents that are also responsive to the application of heat such as those made out of thermoset plastic may be deployed. Increasing evidence shows that the application of heat during an angioplasty procedure can substantially improve the results and decrease the chance of restenosis. In FIG. 15, a catheter 200 incorporating the heating elements is inserted into a vessel 202 and positioned adjacent an obstruction 204 with a shape memory metal stent 206 surrounding the balloon portion of the catheter. Heat is applied to thin film heating elements 208, 210 and 212 located on the exterior of the balloon. Balloon dilatation further expands stent 206 against tissue, with piezoelectric transducers (not shown) employed if desired to insure sufficient radial expansion of the stent. The shape memory metal stent 206 expands and contacts the vessel wall. Because the heat is monitored, the physician may adjust the heat at certain locations as the stent 206 is deployed. Once the stent is deployed, the balloon chambers may be deflated and the balloon catheter removed from the vessel.

Figure 16:
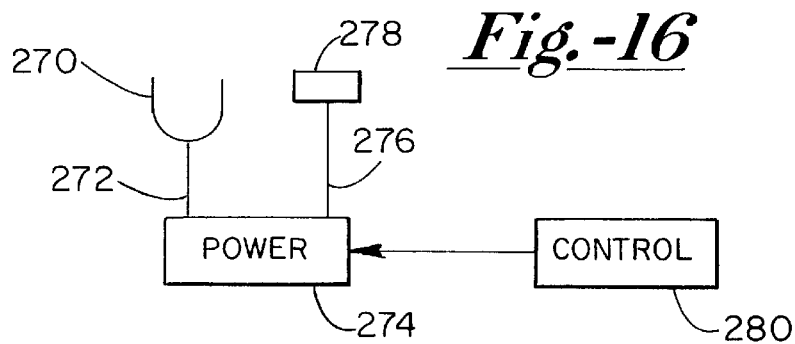
FIG. 16 is a schematic view of alternative circuit for heating the thin film heater

FIG. 16 illustrates an alternative circuit for heating the thin film heat film 270. RF ohmic heating can be provided as an alternative if an indifferent electrode is used. When using ohmic heating, the heating element is sputter coated with a conductive metal such as platinum. A conductor 272 connects the heating thin film with an RF power supply 274. A second conductor 276 couples the power supply and an indifferent electrode 278. The indifferent electrode preferably is an electrode plate typically applied to the back of the patient. The power supply provides an RF signal to the heating element via conductor 272. The signal returns to the power supply via conductor 276. Between the heating element 270 and indifferent electrode 278 current flows through body tissue. Consequently Ohmic heating is the primary factor in raising the temperature of the tissue to the predetermined or desired level. A controller 280 governs power supply 274 to provide the appropriate current to the heating element 270. While not shown in FIG. 16, a thermocouple sensing element can be mounted at the heating thin film to sense the temperature of the thin film and adjacent tissue, and provide feedback to controller 280.

Figure 17:
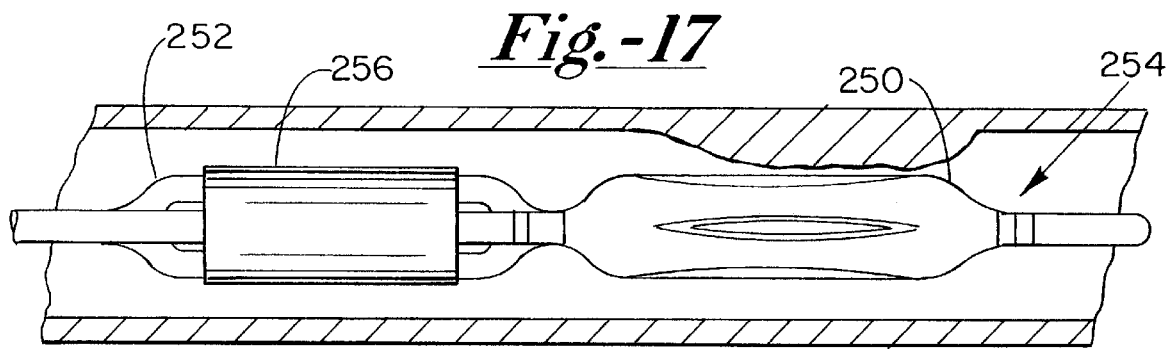
FIG. 17 is an enlarged view of the distal end of a second alternative embodiment utilizing two balloons.

An additional alternative of this balloon catheter incorporates two balloons and is shown in FIG. 17. A first balloon 250 is located at the distal end. A second balloon 252 is located just proximal from the first balloon. Balloons 250 and 252 can be substantially identical. In operation, the catheter is inserted placing the first balloon 250 at the occluded site 254. The first balloon 250 is then inflated to open up the occluded area. The first balloon is deflated and the catheter is advanced placing the second balloon 252 carrying a stent 256 at the lesion site. The second balloon 252 is inflated to deploy the stent 256. Alternatively, the proximal balloon can carry a series of piezoelectric thin film transducers employed in concert as a phased coupled array for ultrasonic imaging. Radiopaque markers are located on the catheter shaft at the distal and proximal ends of the balloons or in the middle to assist the physician in positioning the balloons in the occluded area.

Figure 18:
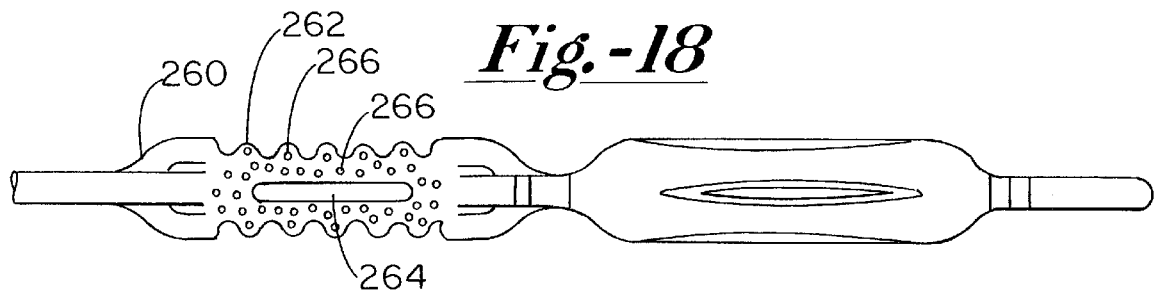
FIG. 18 is an enlarged view of the distal end of a third alternative embodiment utilizing two balloons, one for drug delivery.

When the two balloon embodiment is utilized, a proximal balloon 260 may be used for drug delivery. The balloon has a reduced diameter area 262 with a helical or stepped configuration as shown in FIG. 18. A thin film heater 264 can be bonded to the reduced diameter area. Perforations 266 in the thin film heater and balloon's surface provide the means for drug delivery at the lesion site. The drugs are commonly carried in the fluid which expands the balloon. Such reduced diameter is not necessary, although it allows the drug to pool inbetween balloon 260 and lesion site. Thus, in use, the distal balloon enlarges the occluded area and then the proximal balloon delivers the drug at the treatment site.

While the disclosure has focused on the treatment of coronary arteries, it is to be appreciated that devices in accordance with the present invention can be used to treat peripheral arteries as well as valves within the heart, the esophagus and fallopian tubes. These principals further can be applied in constructing and utilizing devices in neurology for the treatment of obstructions in the carotid arteries. The heating of the balloon and the custom application of pressure during the angioplasty procedure is believed to reduce the incidence of restenosis.

I claim:

1. A balloon catheter including:

an elongate and pliable catheter tubing having a proximal end and a distal end;

a dilatation balloon fixed to the catheter tubing near the distal end, said dilatation balloon including an interior wall means for dividing the balloon into a plurality of dilatation compartments adjacent one another and arranged angularly about the catheter tubing, each of the dilatation compartments being fluid tight and in fluid isolation from the other compartments, said dilatation balloon further including an exterior wall means composed of respective outer wall portions of the dilatation compartments, said exterior wall means (i) defining an outer transverse profile of the dilatation balloon and (ii) being adapted to form a surface engagement with a tissue wall segment surrounding the balloon when the compartments are dilatated, said balloon profile assuming a nominal shape when all of the dilatation compartments are subject to the same pressure;

a balloon dilatation means for supplying a fluid under pressure individually to said dilatation compartments; said dilatation means controllable to adjust the dilatation pressures to different values in at least first and second selected ones of the dilatation compartments, to controllably alter said balloon profile toward conformity with a profile of the tissue wall segment when dilatating the balloon toward and into said surface engagement; and a pressure sensing means, mounted to said exterior wall means and adapted for positioning between the exterior wall means and said tissue wall segment during said surface engagement, for measuring the pressure between the dilatation balloon and the tissue wall segment.

2. The balloon catheter of claim 1 further including:

a heating means proximate said exterior wall means, for heating the tissue wall segment proximate the heating means when the exterior wall means and tissue wall segment are in said surface engagement.

3. The balloon catheter of claim 2 wherein:

said heating means comprises at least one thin film resistive heating element mounted to the exterior wall means.

4. The balloon catheter of claim 3 wherein:

said heating means further includes a bifilar lead including at least two wires, one wire connected to each of the opposite ends of the heating element.

5. The balloon catheter of claim 3 wherein:

said heating means further includes an indifferent electrode spaced apart from the heating element, a first conductor connected to the heating element, and a second conductor connected to the indifferent electrode.

6. The balloon catheter of claim 2 wherein:

said heating means comprises a plurality of heating elements mounted to said exterior wall means in circumferentially spaced apart relation about the dilatation balloon.

7. The balloon catheter of claim 1 wherein:

said dilatation balloon surrounds the catheter tubing and consists of four of said dilatation compartments, each compartment extending 90 degrees circumferentially about the catheter tubing.

8. The balloon catheter of claim 7 wherein:

said interior wall means include single partition walls shared by adjacent ones of the dilatation compartments.

9. The balloon catheter of claim 7 wherein:

said interior wall means and said exterior wall means are formed by a continuous sheet.

10. The balloon catheter of claim 1 wherein:

said balloon dilatation means includes a plurality of balloon inflation lumens formed in said catheter tubing, each of the balloon inflation lumens open to the proximal end of the catheter tubing, extending distally through the catheter tubing and open to an associated one of said balloon compartments.

11. The balloon catheter of claim 10 wherein:

said balloon dilatation means further includes a source of a fluid under pressure near the proximal end of the catheter tubing in fluid communication with the balloon inflation lumens near the proximal end of the catheter tubing, and a plurality of pressure regulating means for individually controlling the respective dilatation pressures of said fluid delivered to the balloon compartments via the associated balloon inflation lumen.

12. The balloon catheter of claim 1 further comprising:

a perfusion lumen contained within the catheter tubing, and open to the exterior of the catheter tubing at first and second locations proximal and distal relative to the balloon, respectively; and wherein said balloon, when dilatated and in said surface engagement, substantially prevents passage of fluids between the catheter tubing and the tissue wall segment.

13. The balloon catheter of claim 12 wherein:

said pressure sensing means includes a plurality of piezoelectric transducing films, one of said films mounted to each one of said outer wall portions.

14. The balloon catheter of claim 1 wherein:

said dilatation balloon is constructed of a compliant material.

15. The balloon catheter of claim 1 wherein:

said dilatation balloon is constructed of an inextensible material.

16. The balloon catheter of claim 1 wherein:

said dilatation compartments extend longitudinally along the catheter tubing.

17. The balloon catheter of claim 1 further including:

multiple perforations through said exterior wall means, adapted for allowing perfusion of a fluid from within each of the dilatation compartments to the tissue wall segment.

18. A balloon catheter comprising:

an elongate and pliable catheter tubing having a proximal end and a distal end;

a dilatation balloon mounted to the catheter tubing at the distal end and surrounding the catheter tubing and having an exterior surface;

a balloon dilatation means for supplying a fluid under pressure to the balloon to dilatate the balloon into a surface engagement with a tissue wall segment surrounding the dilatation balloon; and a pressure sensing means mounted to an exterior surface of the dilatation balloon and disposed between the dilatation balloon and the tissue wall segment, said pressure sensing means being compressible to indicate a pressure between the dilatation balloon and the tissue wall segment.

19. The balloon catheter of claim 18 wherein:

said pressure sensing means comprises a plurality of piezoelectric pressure transducing films spaced apart from one another circumferentially with respect to an axis running lengthwise of said catheter tubing in the region of the dilatation balloon.

20. The balloon catheter of claim 19 wherein:

said dilatation balloon includes an interior wall means for dividing the balloon into a plurality of fluid tight compartments in fluid isolation from one another, and an exterior wall means, composed of respective outer wall portions of the balloon compartments cooperating to provide said balloon exterior surface; and wherein said plurality of piezoelectric transducing film includes one piezoelectric transducing film mounted to each of the outer wall portions, each of the piezoelectric transducing films providing a pressure indication unique to its location between the dilatation balloon and the tissue wall segment.

21. The balloon catheter of claim 20 wherein:

said balloon dilatation means includes a plurality of balloon inflation lumens mounted within the catheter tubing, each one of the balloon inflation lumens being uniquely associated with one of the balloon compartments and in fluid communication with its associated balloon compartment;

a source of a fluid under pressure; and a control means for coupling the source and the balloon inflation lumens, operable to selectively and individually set the fluid pressures in the respective pairs of balloon inflation lumens and compartments.

22. The balloon catheter of claim 19 further including:

a heating means mounted to said balloon exterior surface, for generating heat and thereby heating the tissue wall segment in the region of the heating means when the dilatation balloon and tissue wall segment are in said surface engagement.

23. The balloon catheter of claim 22 further including:

a heat responsive stent plastically deformed to a reduced-radius state in surrounding relation to the dilatation balloon;

wherein said heat responsive stent, responsive to heat generated by said heating means, tends to return to an enlarged radius state in which the heat responsive stent is adapted to become contiguous with and at least slightly radially expand the tissue wall segment.

24. The balloon catheter of claim 19 wherein:

said plurality of piezoelectric transducing films includes one piezoelectric transducing film mounted to each of the outer wall portions, each of the piezoelectric transducing films providing a pressure indication unique to its location between the dilatation balloon and the tissue wall segment.

25. The balloon catheter of claim 18 which:

said pressure sensing means comprises a plurality of enclosed fluid tight tubes spaced apart from one another circumferentially about the dilation balloon and containing a fluid, each of the tubes being compressible to alter the pressure of the fluid it contains.

26. A balloon catheter of claim 25 wherein:

said plurality of enclosed fluid filled tubes includes one fluid filled tube mounted to each of the outer wall portions, each of the fluid filled tubes providing a pressure indication unique to its location between the dilatation balloon and the tissue wall segment.

27. The balloon catheter of claim 18 wherein:

said pressure sensing means includes a plurality of compliant enclosed fluid filled tubes, said tubes having distal ends mounted to said balloon exterior surface.

28. A balloon catheter comprising:

an elongate and pliable catheter tubing having a proximal end and a distal end;

a dilatation balloon mounted to the catheter tubing at the distal end and surrounding the catheter tubing and having an exterior surface;

a balloon dilatation means for supplying a fluid under pressure to the balloon to dilatate the balloon into a surface engagement with a tissue wall segment surrounding the dilatation balloon; and a pressure sensing means mounted to an exterior surface of the dilatation balloon and disposed between the dilatation balloon and the tissue wall segment, said pressure sensing means being compressible to indicate a pressure between the dilatation balloon and the tissue wall segment, said pressure sensing means comprises a plurality of piezoelectric pressure transducing films spaced apart from one another circumferentially with respect to an axis running lengthwise of said catheter tubing in the region of the dilatation balloon;

a heating means mounted to said balloon exterior surface, for generating heat and thereby heating the tissue wall segment in the region of the heating means when the dilatation balloon and the tissue wall segment are in said surface engagement, wherein said heating means comprises at least one thin film resistive heating element mounted to the exterior surface.

29. The balloon catheter of claim 28 further including:

a means for monitoring the temperature proximate said resistive heating element.

30. The balloon catheter of claim 28 wherein:

said heating element comprises a dielectric sheet and a thin film resistive pattern formed on the sheet.

31. The balloon catheter of claim 28 wherein:

the heating means comprises a plurality of heating elements mounted to said exterior surface in circumferentially spaced apart relation about the dilatation balloon.

32. A balloon catheter comprising:

an elongate and pliable catheter tubing having a proximal end and a distal end;

a dilatation balloon mounted to the catheter tubing at the distal end, extended lengthwise of the catheter and surrounding the catheter tubing;

a balloon dilatation means for supplying a fluid under pressure to the balloon to dilatate the balloon into a surface engagement with a tissue wall segment surrounding the dilatation balloon; and a piezoelectric thin film arrangement including least one piezoelectric thin film mounted to an exterior surface of the dilatation balloon and adapted to be disposed between the dilatation balloon and the tissue wall segment.

33. The balloon catheter of claim 32 further including:

a signaling means for providing an ultrasonic signal to the piezoelectric thin film arrangement, for generating an ultrasound image of tissue proximate the dilatation balloon.

34. The balloon catheter of claim 33 wherein:

said signaling means includes a bifilar conductor means coupled to the piezoelectric thin film arrangement and extended to the proximal end of the catheter tubing.

35. The balloon catheter of claim 32 further including:

a means for sensing a voltage difference across a thickness of the piezoelectric film arrangement as an indication of a pressure between the tissue wall segment and the dilatation balloon.

36. The balloon catheter of claim 32 wherein:

said piezoelectric film arrangement comprises a plurality of piezoelectric thin films circumferentially spaced apart from one another to surround the dilatation balloon.

37. The balloon catheter of claim 32 wherein:

said dilatation balloon includes a first wall means for dividing the balloon into a plurality of fluid tight compartments in fluid isolation from one another; and wherein said piezoelectric thin film arrangement includes a plurality of piezoelectric thin films, a different one of the thin films being adjacent each of the compartments.

38. A balloon catheter, comprising:

an elongate and pliable catheter tubing having a proximal end and a distal end;

a dilatation balloon mounted to the catheter tubing at the distal end, extended lengthwise of the catheter and surrounding the catheter tubing;

a balloon dilatation means for supplying a fluid under pressure to the balloon to dilatate the balloon into a surface engagement with a tissue wall segment surrounding the dilatation balloon;

a piezoelectric thin film arrangement including at least one piezoelectric thin film mounted to an exterior surface of the dilatation balloon and adapted to be disposed between the dilatation balloon and the tissue wall segment; and a means for sensing a voltage difference across a thickness of the piezoelectric film arrangement as an indication of a pressure between the tissue wall segment and the dilatation balloon, said sensing means includes a first bifilar conductor means including two wires coupled to opposite sides of the piezoelectric film arrangement and extended to the proximal end of the catheter tubing.

39. The balloon catheter of claim 38 further including:

a signaling means for providing an ultrasonic signal to the piezoelectric film arrangement for generating an ultrasound image of tissue proximate the piezoelectric film arrangement.

40. The balloon catheter of claim 39 wherein:

said signaling means includes a second bifilar conductor means coupled to the piezoelectric film arrangement and extended to the proximal end of the catheter tubing.

41. The balloon catheter of claim 39 further including:

a multiplexing means near the proximal end of the catheter tubing, for alternatively: using the first bifilar conductor means to sense the voltage difference; and using the first bifilar conductor means to provide the ultrasonic signal to the piezoelectric film arrangement.

42. The balloon catheter of claim 39 wherein:

said piezoelectric film arrangement comprises a plurality of piezoelectric thin film transducers spaced apart from one another circumferentially and surrounding the dilatation balloon.

43. A balloon catheter comprising:

an elongate and pliable catheter tubing having a proximal end and a distal end;

a dilatation balloon mounted to the catheter tubing at the distal end, extended lengthwise of the catheter and surrounding the catheter tubing;

a balloon dilatation means for supplying a fluid under pressure to the balloon to dilatate the balloon into a surface engagement with a tissue wall segment surrounding the dilatation balloon; and a compliant fluid filled tube arrangement including at least one enclosed compliant fluid filled tube mounted to an exterior surface of the dilatation balloon and adapted to be disposed between the dilatation balloon and the tissue wall segment.

44. The balloon catheter of claim 43 further including:

a means for sensing a pressure difference within the at least one enclosed compliant fluid filled tube as an indication of the pressure between the tissue wall segment and the dilatation balloon.

45. A balloon catheter comprising:

an elongate and pliable catheter tubing having a proximal end and a distal end;

a dilatation balloon mounted to the catheter tubing at the distal end, extended lengthwise of the catheter and surrounding the catheter tubing;

a balloon dilatation means for supplying a fluid under pressure to the balloon to dilatate the balloon into a surface engagement with a tissue wall segment surrounding the dilatation balloon;

a plurality of compliant fluid filled tubes mounted to an exterior surface of the dilatation balloon and adapted to be disposed between the dilatation balloon and the tissue wall segment; and a means for sensing a pressure difference within each compliant fluid filled tubes as an indication of the pressure between the tissue wall segment and the dilatation balloon, wherein said pressure sensing means includes a digital pressure measuring device for measuring the internal pressure of each said compliant fluid filled tube.

46. A balloon catheter comprising:

an elongate and pliable catheter tubing having a proximal end and a distal end;

a dilatation balloon having an exterior surface, said dilatation balloon mounted to the catheter tubing at the distal end and extending lengthwise along the catheter tubing;

a plurality of thin film resistive heating elements mounted to said exterior surface of the dilatation balloon;

a balloon dilatation means for supplying a fluid under pressure to the balloon to dilatate the balloon into a surface engagement with a tissue wall segment surrounding the dilatation balloon, with said resistive heating elements disposed between the dilatation balloon and the tissue wall segment; and a plurality of piezoelectric thin film pressure transducers mounted to said exterior surface, with a different one of the pressure transducers being adjacent each of the resistive heating elements.

47. The balloon catheter of claim 46 wherein:

said dilatation balloon includes a wall means for dividing the balloon into a plurality of fluid tight compartments in fluid isolation from one another; and said plurality of thin film resistive heating elements include a different one of said heating elements mounted adjacent each of said compartments.

48. A balloon catheter comprising:

an elongate and pliable catheter tubing having a proximal end and a distal end, and a dilatation balloon having an exterior surface, said dilatation balloon mounted to the catheter tubing at the distal end and extending lengthwise along the catheter tubing;

a piezoelectric thin film mounted to said exterior surface of the dilatation balloon;

a thin film resistive heating element mounted to the exterior surface and adjacent the piezoelectric thin film; and a balloon dilatation means for supplying a fluid under pressure to the balloon to dilatate the balloon into a surface engagement with a tissue wall segment surrounding the dilatation balloon, with the piezoelectric thin film and the thin film resistive heating element disposed between the dilatation balloon and the tissue wall segment.

49. A balloon catheter comprising:

an elongate and pliable catheter tubing having a proximal end and a distal end, and a dilatation balloon having an exterior surface, said dilatation balloon mounted to the catheter tubing at the distal end and extending lengthwise along the catheter tubing;

a piezoelectric thin film mounted to said exterior surface of the dilatation balloon;

a thin film resistive heating element mounted to the exterior surface and adjacent the piezoelectric thin film;

a balloon dilatation means for supplying a fluid under pressure to the balloon to dilatate the balloon into a surface engagement with a tissue wall segment surrounding the dilatation balloon, with the piezoelectric thin film and the thin film resistive heating element disposed between the dilatation balloon and the tissue wall segment; and a means for sensing a voltage difference across a thickness of the piezoelectric thin film as an indication of pressure between the tissue wall segment and the dilatation balloon.

* * * * *